United States Patent [19]

Brennan

[11] 4,448,997

[45] May 15, 1984

[54] PREPARATION OF LINEAR POLYETHYLENEPOLYAMINES WITH AN ALUMINUM PHOSPHATE CATALYST

[75] Inventor: Michael E. Brennan, Austin, Tex.

[73] Assignee: Texaco Inc., White Plains, N.Y.

[21] Appl. No.: 453,841

[22] Filed: Dec. 27, 1982

Related U.S. Application Data

[63] Continuation-in-part of Ser. No. 283,713, Jul. 16, 1981, abandoned.

[51] Int. Cl.³ .............................................. C07C 85/06
[52] U.S. Cl. .................................................... 564/479
[58] Field of Search ......................................... 564/479

[56] References Cited

U.S. PATENT DOCUMENTS

| | | | |
|---|---|---|---|
| 3,297,701 | 1/1967 | Brader et al. | 260/268 |
| 3,342,820 | 9/1967 | Brader | 260/268 |
| 4,014,945 | 3/1977 | Zimmerachied | 260/635 E |
| 4,036,881 | 7/1977 | Brennan et al. | 260/583 P |
| 4,044,053 | 8/1977 | Brennan et al. | 260/583 P |
| 4,103,087 | 7/1978 | Brennan | 544/78 |
| 4,210,560 | 7/1980 | Kehl | 252/437 |

FOREIGN PATENT DOCUMENTS 528987 11/1940 United Kingdom ............... 564/479

*Primary Examiner*—Paul F. Shaver
*Attorney, Agent, or Firm*—Robert A. Kulason; Jack H. Park; Harold J. Delhommer

[57] ABSTRACT

A method of preparing predominantly linear polyethylenepolyamines from ethylenediamine and monoethanolamine reactants with an aluminum phosphate catalyst prepared from alumina, phosphoric acid, ammonium hydroxide and water is disclosed.

8 Claims, No Drawings

PREPARATION OF LINEAR POLYETHYLENEPOLYAMINES WITH AN ALUMINUM PHOSPHATE CATALYST

TECHNICAL FIELD OF THE INVENTION

This is a continuation-in-part of U.S. patent application Ser. No. 283,713, filed July 16, 1981, now abandoned.

This invention relates to the preparation of predominantly linear polyethylenepolyamines from the starting reagents of ethylenediamine and monoethanolamine in the presence of a aluminum phosphate catalyst.

BACKGROUND OF THE INVENTION

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominantly non-cyclic polyethylenepolyamine compounds are obtained from this process with varying yields of heterocyclic amines. The large amounts of energy required to produce the reactants as well as the difficult separation procedures required to recover the more valuable linear polyethylenepolyamines diminish the usefulness of the ethylene dichloride process. The hydrohalide salts of ammonia and the polyethylenepolyamine products must also undergo difficult and time consuming caustic neutralization to yield the free polyethylenepolyamines.

The production of polyethylenepolyamines from the starting reactants of an alkyleneamine and an alkanolamine is a process that has come under recent research scrutiny. Two feasible reactants for this process in terms of cost and availability are ethylenediamine and monoethanolamine. Unfortunately, reaction of these two reagents tends to produces copious quantities of cyclic products diminishing the possible yield of the more valuable and sought after linear polyethylenepolyamines.

When catalyzed, the reaction of monoethanolamine and ethylenediamine yields numerous products. The most desirable products are the predominantly linear polyethylenepolyamines. Products that are less desirable include such cyclic compounds as:

AEP—N-(2-aminoethyl)piperazine
DiAEP—diaminoethylpiperazine
PEEDA—piperazinoethylethylenediamine It is believed that this propensity to create myriad products is due to the primary amine nature of both monoethanolamine and ethylenediamine, which offer considerably more reactive hydrogen sites and product possibilities than tertiary or secondary amines.

It is well known that different classes of amines—primary, secondary and tertiary—generally react in different ways. In many reactions, the final products depend upon the number of hydrogen atoms attached to the nitrogen atom, and hence are different for amines of different classes. See, R. Morrison and R. Boyd, *Organic Chemistry*, Allyn and Bacon, Inc., New York (3rd ed. 1973) p. 728. Chemists have taken advantage of the differences in reaction between amine classes to develop several tests for distinguishing between primary, secondary and tertiary amines; most notably, the isocyanide test for primary amines, enamine formation from aldehydes and ketones for secondary amines, the Hinsberg reaction, hydrogen peroxide or peracid reactions, and nitrous acid reactions with all three classes of amines. See, *Kirk-Othmer Encyclopedia of Chemical Technology*, John Wiley & Sons, New York (3rd ed. 1978) Vol. 2, pp. 272, 275 and C. Noller, *Chemistry of Organic Compounds*, W. B. Saunders Co., Philadelphia (3rd ed. 1965) pp. 260,509.

U.S. Pat. No. 4,044,053 discloses a process for preparing polyalkylenepolyamines from an alkyleneamine and ethylene glycol in the presence of a phosphorus-containing compound. However, neither the unique aluminum phosphate catalyst of the claimed invention, nor the surprising results achieved thereby, is disclosed in said patent. U.S. Pat. No. 4,036,881 discloses a method of reacting an alkyleneamine with an alkanolamine in the presence of a phosphorus-containing compound of the group consisting of acidic metal phosphates, phosphoric acid compounds and alkyl or aryl phosphate esters. Although aluminum phosphate is mentioned as a catalyst, it is not the aluminum phosphate catalyst prepared in accordance with the invention. The process of '881 yields a relatively lower conversion to linear polyethylenepolyamines when the disclosed catalyst is employed, rather than the catalyst prepared according to the present invention.

Aluminum phosphate has been thought to be a compound which would catalyze reactions to produce predominantly heterocyclic rather than linear products. U.S. Pat. No. 3,297,701 teaches using aluminum phosphate to catalyze ethanolamines and polyethylenepolyamines to yield cyclic compounds. U.S. Pat. No. 3,342,820 also discloses the use of an aluminum phosphate catalyst for the preparation of heterocyclic compounds such as triethylenediamine.

U.S. Pat. No. 4,103,087 issued to Brennan provides a third example of an aluminum phosphate catalyst for producing heterocyclic product compounds. This Brennan patent discloses a process for making a di-(N,N-disubstituted amino) alkane compound containing a morpholine substituent from a tertiary aminoalkanol and a secondary amine. Because the Brennan reference reacts a tertiary amine with a secondary amine, the reactions and products are relatively simple compared with the numerous additional reactions and myriad byproducts created when two primary amines are reacted according to the present invention. Indeed, the Brennan reference does not discuss at all the subject of the present invention, the preparation of linear polyethylenepolyamines. It is instead concerned with the preparation of morpholine compounds. Thus, it would be difficult to predict the numerous byproducts formed from the reaction of two primary amines from knowledge of the reaction between a tertiary and a secondary amine having different compositions. At best, a survey of the prior art would lead a skilled chemist to the conclusion that aluminum phosphate compounds employed as catalysts yield predominantly heterocyclic products.

SUMMARY OF THE INVENTION

A novel method of preparing predominantly linear polyethylenepolyamines from ethylenediamine and monoethanolamine reactants employing an aluminum phosphate catalyst is disclosed. The aluminum phosphate catalyst used in the claimed invention yields a greater proportion of the more valuable linear polyethylenepolyamines than the prior art processes. The catalyst is prepared by mixing and reacting alumina with phosphoric acid, adding water to the reaction mixture followed by the addition of ammonium hydroxide. The aluminum phosphate product is then separated, purified and calcined.

DETAILED DESCRIPTION

The invention is an improved method of producing predominantly linear polyethylenepolyamines such as diethylenetriamine, triethylenetetramine, tetraethylenepentamine and pentaethylenehexamine from the reaction of ethylenediamine and monoethanolamine employing an aluminum phosphate catalyst. The production of larger percentages of less valuable heterocyclic amines is a problem which afflicts the use of other catalysts, including aluminum phosphate catalysts not prepared by the method of this invention. Inventor is unaware of precise structural differences between the aluminum phosphate catalyst employed herein and previous aluminum phosphate catalysts which have been tried in such reactions, but is cognizant of substantially higher rates of conversion to linear polyethylenepolyamines with the present process using an aluminum phosphate catalyst.

The present aluminum phosphate compound catalyzes the reaction of ethylenediamine and monoethanolamine at a temperature of from about 200° C. to about 400° C., preferably from about 300° C. to about 350° C. and a pressure of from about 700 to about 1400 psig. The molar ratio of ethylenediamine to monoethanolamine ranges from about 1:2 to about 5:1, preferably from about 1 to about 2 moles of ethylenediamine per mole of monoethanolamine.

The quantity of aluminum phosphate employed as the catalyst in the invention is an effective amount which can vary widely depending upon the reactivity desired, the reactants present and particular reaction conditions employed. Usually the catalytically effective amount is within the range of from about 0.01 to about 20.0 weight percent, based upon the weight of monoethanolamine reactant present before reaction. Preferably, the catalyst is employed in an amount ranging from about 5.0 to about 15.0 weight percent, monoethanolamine basis.

To prepare the catalyst employed in the method of this invention, about 5 to 10 moles of 85% phosphoric acid is mixed and reacted with each mole of hydrated alumina at atmospheric pressure and a temperature of from about 80° to 120° C. The hydrated alumina used in the invention has the structure $Al_2O_3.3H_2O$ and is sold under the trademark RH-31F by Reynolds Chemicals. Analysis of one sample yielded 65.25% $Al_2O_3$ 0.13% $Na_2O$, 0.008% $SiO_2$, 0.003% $Fe_2O_3$, 0.02% free water (% on dry basis with bulk density of about 60–80 lbs/ft$^3$). But other alumina compounds, hydrated or not, may be employed.

Sufficient water is added to the phosphoric acid and alumina reaction mixture to yield a pH of about 2 to 3 for the clear and colorless reaction solution. If non-hydrated alumina is used, an additional quantity of water must be added to the reaction mixture to obtain the proper pH. Although the molar ratio of 85% phosphoric acid to alumina ranges from about 5 to 10 moles per mole of alumina, it is preferred that about 6 moles of phosphoric acid be added per mole of alumina to provide a sufficient excess of phosphoric acid.

A 30% ammonium hydroxide solution is then added to the alumina-phosphoric acid reaction mixture to yield a white precipitate. Addition of the 30% ammonium hydroxide solution is continued until precipitate formation ceases and the pH of the resulting mixture is about 5 to 6. The precipitate is separated from the reaction mixture by means such as suction filtration and purified by several water and methanol washes. After the drying of the precipitate in a vacuum desiccator, the precipitate is calcined in an oven for a time ranging from about 4 to about 25 hours at a temperature of from about 200° C. to about 750° C.

For unknown reasons, the disclosed process of preparing polyethylenepolyamines with the disclosed aluminum phosphate catalyst is substantially more selective to the production of the more valuable linear polyethylenepolyamines than cyclic polyethylenepolyamines. This is brought out by the substantially higher percentages of conversion to the linear polyethylenepolyamines by the claimed process than the same process with other aluminum phosphate catalysts as will be seen from later examples. Although Inventor is unaware of the structural differences between the claimed aluminum phosphate catalyst and other aluminum phosphate catalysts which have been employed in the production of polyethylenepolyamines, the greater conversion ratios emphasize that there is a difference between the claimed aluminum phosphate catalyst and aluminum phosphate catalysts prepared by other methods.

It has been unexpectedly discovered that calcination at temperatures of from about 250° C. to about 750° C. also has significant effects upon the selectivity of the aluminum phosphate catalyst to the production of linear polyethylenepolyamines. Calcination at these temperatures has been found to increase the catalytic activity of the aluminum phosphate and result in a higher conversion to the higher molecular weight, linear polyethylenepolyamines such as triethylenetetramine, tetraethylenepentamine and pentaethylenehexamine. This is illustrated in later examples.

The aluminum phosphate catalyst of this invention has been found, by analysis, to contain approximately 20 to 27 weight percent phosphorus, 15 to 19 weight percent aluminum, 2 to 3 weight percent nitrogen and 20 to 200 ppm sodium.

There are many compounds which can be formed from the reaction of the primary amine compounds, ethylenediamine and monoethanolamine, besides the preferred linear polyethylenepolyamines such as diethylenetriamine, triethylenetetramine, tetraethylenepentaimine and pentaethylenehexamine. Less desirable cyclics and other compounds, such as piperazine, N-(2-aminoethyl)ethanolamine and N-(2-aminoethyl)piperazine, are also formed. It is believed that the primary amine nature of the starting reactants offers more possible reaction sites, and thus, more byproducts than secondary or tertiary amine reactants would produce.

The more desired linear polyethylenepolyamines can be easily recovered from the reaction product mixture by conventional methods such as distillation. Such distillation recovery methods are well known in the art. An outstanding advantage of the claimed invention is that the lower molecular weight polyethylenepolyamines recovered from the reaction mixture can be further reacted with monethanolamine to produce a larger percentage of the higher molecular weight linear polyethylenepolyamines.

The following examples will further illustrate the preparation of predominantly linear polyethylenepolyamines from ethylenediamine and monoethanolamine by the use of the claimed process. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed and the products obtained have been abbreviated in the following examples and tables. The abbreviations employed for these various compounds are:

EDA—ethylenediamine
MEA—monoethanolamine
DETA—diethylenetriamine
TETA—triethylenetetramine
TEPA—tetraethylenepentamine
PEHA—pentaethylenehexamine
AEEA—N-(2-aminoethyl)ethanolamine
AEP—N-(2-aminoethyl)piperazine
DiAEP—diaminoethylpiperazine
PEEDA—piperazinoethylethylenediamine
NTEA—nitrilotrisethylamine

EXAMPLE 1

A 250 milliliter round bottom flask was charged with 67.6 grams (0.43 moles) of hydrated alumina ($Al_2O_3.3H_2O$) and 279.4 grams (2.42 moles) of 85% phosphoric acid at atmospheric pressure. The concentrated 85% phosphoric acid was added in several portions. The reaction mixture remained at ambient temperature for a short time. Then the temperature rapidly rose to about 120° C. before leveling off. A viscous, homogeneous solution resulted. The hot reaction solution was poured with stirring into 750 milliliters of distilled water to get a clear and colorless solution with a pH of approximately 2 to 3.

A 30% ammonium hydroxide solution was added which instantly yielded a white precipitate. Addition of ammonium hydroxide was continued until precipitate formation ceased. Suction filtration was employed to separate the white precipitate from the reaction solution. The precipitate was then washed well with distilled water (7 washes of 500 milliliters each) and then washed with methanol (4 washes of 500 milliliters each). After washing, the precipitate weighed 589 grams. The crude precipitate was then dried in a vacuum desiccator at 80°–100° C. for 16 hours, which yielded 173 grams of dry precipitate. One-half of the dried precipitate was calcined in an oven at 250° C. for 7 hours which reduced the precipitate to 73.7 grams. Atomic absorption spectroscopy and analysis for nitrogen by the Kjeldahl procedure yielded the following figures:

|  | Weight % | | | |
| --- | --- | --- | --- | --- |
|  | P | Al | N | Na (ppm) |
| Non-calcined | 23.7 | 12.45 | 6.05 | 194 |
| Calcined at 250° C. | 27.8 | 15.6 | 2.57 | 172 |
| Theoretical for AlPO$_4$ | 25.4 | 22.1 | | |

The two catalysts (calcined and non-calcined) were employed to catalyze the reaction of ethylenediamine and monoethanolamine. A nitrogen-pureged autoclave was charged with a solution of 225 grams (3.75 moles) of ethylenediamine and 229 grams (3.75 moles) of monoethanolamine and 22.9 grams (10.0 wt. %, basis MEA) of one of the catalysts. The autoclave was padded with nitrogen, sealed and heated to 315° C. for 2 hours at a pressure of from 700 to 1400 psig. After cooling, the liquid product mixture was analyzed by gas-liquid chromatography, atomic absorption spectroscopy and Karl Fisher titration for water. The results are reproduced in Table 1.

TABLE 1

|  | Catalyst | |
| --- | --- | --- |
|  | Non-Calcined | Calcined at 250° C. |
| % H$_2$O(KF)[1] | 8.81 | 10.3 |
| AA[2] ppm | | |
| Na | 1.3 | 4.9 |
| Al | <3.1 | <3.9 |
| P | <5.2 | <6.4 |
| Glc, A %[3] | | |
| Lights | 2.6 | 2.8 |
| H$_2$O | 9.1 | 12.4 |
| EDA | 15.4 | 10.2 |
| MEA | 27.6 | 21.6 |
| Piperazine | 1.6 | 2.5 |
| DETA | 21.2 | 17.7 |
| AEEA | 3.0 | 2.6 |
| AEP/HEP | 1.7 | 3.3 |
| NTEA | 0.6 | 0.9 |
| TETA | 11.2 | 13.1 |
| DiAEP | 0.4 | 0.9 |
| PEEDA | 0.5 | 1.3 |
| TEPA | 3.9 | 7.0 |
| PEHA | 0.8 | 2.9 |
| % Conversion, | | |
| EDA | 69.0 | 79.0 |
| MEA | 45.0 | 56.2 |
| Total | 56.9 | 67.5 |
| DETA/Piperazine | 13.2 | 7.1 |
| % Noncyclic, | | |
| TETA isomers | 92.5 | 85.9 |
| TEPA isomers | 92.4 | 87.3 |

[1]Karl Fischer Titration
[2]Atomic Absorption Spectroscopy
[3]Gas Liquid Chromotography, Area Percent

EXAMPLE 2

A 2 liter beaker was charged with the same quantities of a hydrated alumina ($Al_2O_3.3H_2O$) and phosphoric acid as in Example 1. The concentrated phosphoric acid was added in several portions over 18 minutes, but the solution remained at about 40° C. even with stirring. The alumina remained insoluble. The reaction mixture was then heated for 1 hour at 50° C. to 120° C. and became a viscous homogeneous solution at 100° C. to 110° C. After cooling to 90° C., 750 milliliters of distilled water were added in three equal portions followed by 150 milliliters of 30% ammonium hydroxide in four portions at 35° C. to 45° C. All of the above reaction steps were conducted at atmospheric pressure.

The white precipitate formed during addition of the ammonium hydroxide was then isolated as in Example 1 and washed and dried in a vacuum desiccator at 80° C. to 112° C. for 11 hours. Two portions of the catalyst were then calcined at difference temperatures, 250° C. for 17 hours and 500° C. for 6 hours resulting in approximately a 30% weight loss for each catalyst. Analysis yielded the following catalyst composition:

|  | Weight % | | | |
| --- | --- | --- | --- | --- |
|  | P | Al | N | Na (ppm) |
| Non-calcined | 17.4 | 9.4 | 5.64 | 65 |
| Calcined at 250° C. | 27.9 | 16.0 | 1.54 | <7.2 |
| Calcined at 500° C. | 29.2 | 16.8 | 0.07 | 12.8 |

The three catalysts were employed in a polyethylenepolyamine synthesis following the procedure of Example 1. Analysis of the polyethylenepolyamine product mixture yielded the results of Table 2.

TABLE 2

| | Catalysts | | |
|---|---|---|---|
| | Non-Calcined | Calcined at 250° C. | Calcined at 500° C. |
| % Conversion, | | | |
| EDA | 65.3 | 80.4 | 79.2 |
| MEA | 43.1 | 59.7 | 56.9 |
| Total | 54.1 | 70.0 | 68.0 |
| DETA/Piperazine | 13.6 | 5.8 | 6.8 |
| % Noncyclic, | | | |
| TETA isomers | 92.5 | 84.0 | 86.9 |
| TEPA isomers | 92.1 | 85.3 | 87.5 |

EXAMPLE 3

Twenty-two one-pound lots of the aluminum phosphate catalyst were prepared following the procedure of Example 1. Each catalyst was made up in a four liter beaker equipped with a mechanical stirrer and 234 grams (1.5 moles) of hydrated alumina, 1038 grams (9.0 moles) of 85% phosphoric acid and 557 milliliters of 30% ammonium hydroxide. In contrast to the previous examples, the alumina-phosphoric acid mixtures exothermed at about 70° C. to 85° C. All catalyst lots were separated and dried as in Example 1 and then calcined to 250° C. for 21 hours. Analysis of the catalysts yielded the average percentage of constituents noted below:

| Weight % | | | |
|---|---|---|---|
| P | Al | N | Na (ppm) |
| 20.4–27.2 | 15.6–18.9 | 2.73–2.78 | 24–134 |

Four of the catalyst lots were employed in the polyethylenepolyamine synthesis of Example 1. Analysis yielded the range of results listed below:

| % Conversion; | |
|---|---|
| EDA | 60.0–77.6 |
| MEA | 39.1–46.2 |
| Total | 50.0–60.3 |
| DETA/Piperazine | 10.4–16.3 |
| % Noncyclic TETA isomers | 91.2–94.9 |
| % Noncyclic TEPA isomers | 91.2–94.5 |

EXAMPLES 4 TO 16

For comparison purposes, a number of commercially available aluminum phosphates as well as several aluminum phosphates prepared in the laboratory following previously disclosed methods of preparation were tested as catalysts in the polyethylenepolyamine synthesis of Example 1. Table 3 identifies the catalysts as well as the percent conversion of the reactants promoted by each catalyst in the polyethylenepolyamine reaction.

Catalyst numbers 4, 10 and 15 were the only catalysts to convert an appreciable percentage of EDA an MEA to polyethylenepolyamines; a conversion percentage of only 25% to 35%. A review of Examples 1, 2 and 3 reveals that every catalyst prepared according to the invention yielded double the reactant conversion to polyethylenepolyamines of the best three catalysts bought commercially or prepared in the laboratory according to the prior art.

TABLE 3

| Catalyst No. | Wt. %, MEA basis | % Conversion | | | DETA/ Piperazine |
|---|---|---|---|---|---|
| | | EDA | MEA | Total | |
| 4 | 10.0 | 29.5 | 39.9 | 34.7 | 16.8 |
| 5 | 20.0 | 16.9 | 23.4 | 20.2 | 25.5 |
| 6 | 25.0 | 12.3 | 27.4 | 19.9 | 16.3 |
| 7 | 50.0 | 5.8 | 10.7 | 8.3 | <21.3 |
| 8 | 20.0 | 14.4 | 3.6 | 9.0 | <43.4 |
| 9 | 10.0 | 10.5 | 23.6 | 17.1 | 22.5 |
| 10 | 10.0 | 22.0 | 28.0 | 25.0 | 12.5 |
| 11 | 10.0 | 5.4 | 13.6 | 9.5 | <22.3 |
| 12 | 10.0 | 4.4 | 8.3 | 6.4 | — |
| 13 | 10.0 | 10.6 | 15.5 | 13.1 | 21.7 |
| 14 | 10.0 | 4.0 | 6.5 | 5.3 | <19.8 |
| 15 | 10.0 | 38.9 | 37.7 | 38.3 | 2.2 |
| 16 | 10.0 | 3.8 | 10.7 | 7.3 | 22.0 |

4 Research Organic/Research Inorganic Chemical Corp.; 11.6 wt. % P, 0.94 wt. % Na. Subject company was unable to reproduce this catalyst preparation. Other supposedly identical samples furnished gave a maximum total conversion of 10%.
5 Girdler Chemical Co., Inc., 49% AlPO$_4$ on alumina; 10.34 wt. % P, 0.13 wt. % Na.
6 Girdler Chemical Co., 41% AlPO$_4$ on alumina; 8.90 wt. % P, 129-152 ppm Na.
7 Girdler Chemical Co., 5% AlPO$_4$ on alumina; 2.08-2.54 wt. % P, 839 ppm Na.
8 Harshaw Chemical Co., Inc. aluminum phosphate; 13.08–16.52 wt. % P, 9.9 wt. % Na.
9 BDH Chemicals, Ltd. (distributed by Gallard-Schlesinger Chem. Mfg. Corp.) AlPO$_4$.xH$_2$O; 18.2 wt. % P, 218 ppm Na.
10 Mallinckrodt 3176; 13.4 wt. % P, 0.52 wt. % Na, 83 ppm K.
11 Laboratory prepared from Al(NO$_3$)$_3$.9H$_2$O + Na$_3$PO$_4$ 12H$_2$O in water; 11.7 wt. % P, 4.1 wt. % Na.
12 Laboratory prepared from Al[OCH(CH$_3$)$_2$]$_3$ + H$_3$PO$_4$ in isopropanol; 18.1 wt. % P.
13 Laboratory prepared from Al(NO$_3$)$_3$.9H$_2$O + (NH$_4$)$_2$HPO$_4$ in water followed by NH$_4$OH precipitation; 8.9 wt. % P.
14 Laboratory prepared from Al(NO$_3$)$_3$.9H$_2$O + NH$_4$OH + H$_3$PO$_4$ in water; 14.7 wt. % P.
15 Laboratory prepared from aluminum powder and 35% H$_3$PO$_4$ according to the procedure of J. C. Brosheer, J. Am. Chem. Soc., Vol. 76, p. 5951 (1954); 23.5 wt. % P, 20.7 wt. % Al, 143 ppm Na.
16 Laboratory prepared "basic" AlPO$_4$ from Al$_2$(SO$_4$)$_3$.16H$_2$O + 2Na$_2$HPO$_4$ + Na$_2$CO$_3$; 18.1 wt. % P, 20.3 wt. % Al, 13.6 wt. % Na according to British Patent No. 649,980, issued Feb. 7, 1951.

The preparation of predominantly linear polyethylenepolyamines by the use of the novel aluminum phosphate catalyst disclosed herein can be performed by varying the basic reactants over several limits. Many variations of the method of this invention will be apparent to those skilled in the art from the foregoing discussion and examples. Variations can be made without departing from the scope and spirit of the following claims.

I claim:

1. A method of preparing linear polyethylenepolyamines from ethylenediamine and monoethanolamine which comprises:

mixing and reacting ethylenediamine with monoethanolamine at a temperature of about 200° to about 400° C. and a pressure of about 700 to about 1400 psig in the presence of a catalytically effective amount of an aluminum phosphate catalyst;

said catalyst prepared by mixing and reacting alumina with phosphoric acid, adding water to the reaction mixture, adding ammonium hydroxide to form a precipitate, continuing the addition of ammonium hydroxide until precipitate formation ceases, and separating the precipitate catalyst from the reaction mixture; and recovering a polyethylenepolyamine product characterized by a relatively large percentage of linear, non-cyclic polyethylenepolyamines.

2. The method of claim 1, wherein about one-half mole to about 5 moles of ethylenediamine per mole of monoethanolamine are mixed and reacted with said monoethanolamine.

3. The method of claim 1, wherein the ethylenediamine and monoethanolamine are mixed and reacted in the presence of from about 5.0 to about 15.0 weight percent of said aluminum phosphate catalyst, based on the amount of monoethanolamine present.

4. The method of claim 1, wherein about 5 moles to about 10 moles of 85% by weight phosphoric acid per mole of alumina are mixed and reacted with said alumina.

5. The method of claim 1, wherein water is added to the phosphoric acid and alumina reaction mixture until the mixture reaches a pH of about 2 to about 3.

6. The method of claim 1, wherein the ethylenediamine and monoethanolamine are mixed and reacted in the presence of said catalyst at a temperature of about 300° to about 350° C.

7. A method of preparing linear polyethylenepolyamines from ethylenediamine and monoethanolamine which comprises:

mixing and reacting about one mole to about two moles of ethylenediamine per mole of monoethanolamine with monoethanolamine at a temperature of about 300° C. to about 350° C. and a pressure of about 700 to about 1400 psig in the presence of from about 5.0 to about 15.0 weight percent aluminum phosphate catalyst, based on the amount of monoethanolamine present;

said catalyst prepared by (a) mixing and reacting 85 wt. % phosphoric acid with hydrated alumina in a molar ratio of about six moles of phosphoric acid per mole of alumina, (b) adding sufficient water to the phosphoric acid and alumina reaction mixture to yield a pH of about 2 to 3 for the mixture, (c) adding a 30% ammonium hydroxide solution to the mixture to form a precipitate and continuing addition of the ammonium hydroxide solution until precipitate formation ceases and the pH of the mixture is about 5 to 6, (d) separating the precipitate from the reaction mixture, isolating and drying the precipitate; and recovering a polyethylenepolyamine product characterized by a relatively large percentage of linear, non-cyclic polyethylenepolyamines.

8. The method of claim 7, wherein the precipitate from the catalyst reaction mixture is calcined in an oven for about 4 to about 25 hours at about 200° C. to about 750° C. after the precipitate is dried.

* * * * *